(12) United States Patent
Bubear

(10) Patent No.: US 11,649,957 B2
(45) Date of Patent: May 16, 2023

(54) VETERINARY LIGHTING APPARATUS

(71) Applicant: CASCO Europe Limited, Horsham (GB)

(72) Inventor: Matthew Bubear, Horsham (GB)

(73) Assignee: CASCO EUROPE LIMITED, Horsham (GB)

( * ) Notice: Subject to any disclaimer, the term of this patent is extended or adjusted under 35 U.S.C. 154(b) by 0 days.

(21) Appl. No.: 17/678,626

(22) Filed: Feb. 23, 2022

(65) Prior Publication Data

US 2022/0268435 A1    Aug. 25, 2022

(30) Foreign Application Priority Data

Feb. 25, 2021   (GB) ..................................... 2102658

(51) Int. Cl.
| | |
|---|---|
| *F21K 9/64* | (2016.01) |
| *F21V 23/04* | (2006.01) |
| *F21Y 115/10* | (2016.01) |
| *F21V 29/70* | (2015.01) |

(52) U.S. Cl.
CPC ................ *F21V 29/70* (2015.01); *F21K 9/64* (2016.08); *F21V 23/04* (2013.01); *F21Y 2115/10* (2016.08)

(58) Field of Classification Search
CPC ......... F21V 23/04; F21K 9/64; F21Y 2115/10
See application file for complete search history.

(56) References Cited

U.S. PATENT DOCUMENTS

| | | | | |
|---|---|---|---|---|
| 8,882,291 | B1 * | 11/2014 | Bourget | ................... F21S 4/20 |
| | | | | 362/249.02 |
| 2012/0002408 | A1 | 1/2012 | Lichten et al. | |
| 2014/0288351 | A1 * | 9/2014 | Jones | .................. A61N 5/0624 |
| | | | | 607/90 |
| 2015/0116997 | A1 | 4/2015 | Tappert et al. | |
| 2017/0041997 | A1 | 2/2017 | Wang | |
| 2017/0290124 | A1 | 10/2017 | Grajcar | |
| 2019/0320627 | A1 | 10/2019 | Lawyer et al. | |

OTHER PUBLICATIONS

Extended European Search Report for EP Patent Application No. 22157296, dated Jul. 15, 2022, 7 pages.
Search Report for GB Patent Application No. 2102658.8, dated Dec. 1, 2021, 3 pages.

* cited by examiner

*Primary Examiner* — Karabi Guharay
(74) *Attorney, Agent, or Firm* — ArentFox Schiff LLP

(57) ABSTRACT

A veterinary lighting apparatus comprising: a heat sink on which are supported a plurality of LEDs for emitting light radiation, wherein the plurality of LEDs comprises at least one white light LED-emitter; at least one blue light LED-emitter; and at least one red light LED-emitter; and an activation means to switch on one or more of the white and/or blue and/or red light LED-emitters.

21 Claims, 2 Drawing Sheets

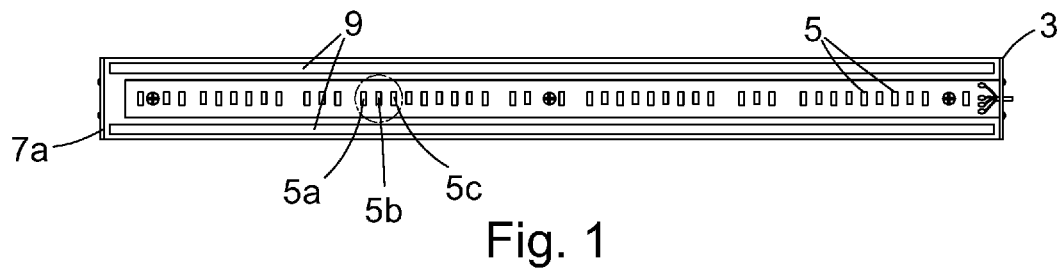
Fig. 1
Fig. 2
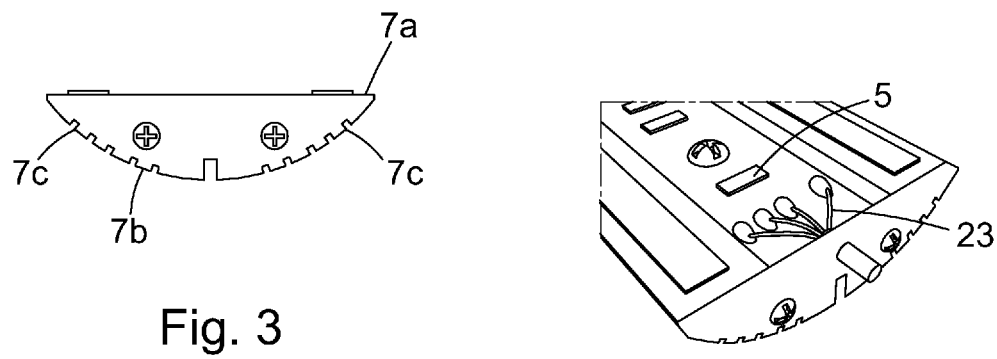
Fig. 3
Fig. 4
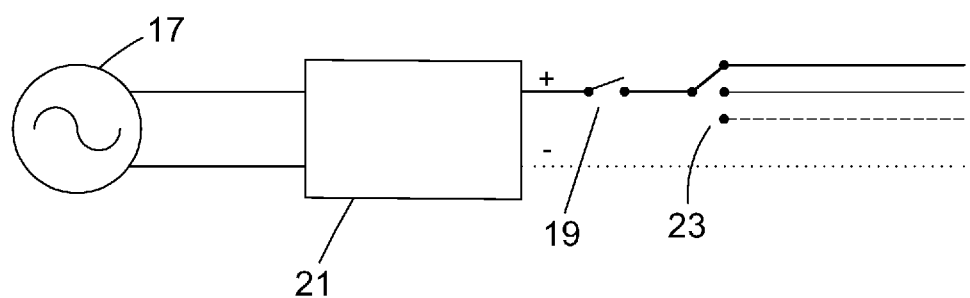
Fig. 5

VETERINARY LIGHTING APPARATUS

CROSS-REFERENCE TO RELATED APPLICATIONS

This application claims priority to GB Application No. GB2102658.8, filed Feb. 25, 2021, the disclosure of which is incorporated by reference in its entirety.

FIELD

The present invention relates to a veterinary lighting apparatus and a method of using a veterinary lighting apparatus.

BACKGROUND

Lighting apparatus used to provide improved artificial lighting to suit the circadian rhythms of humans is known whereby the impact of the light emitted is selected to keep "in tune" with the "body clock" of the human user. The lighting apparatus is used to create lighting conditions that are conducive to the health of the user and prevent disruption to melatonin production, which can be a problem with harsh lighting, such as lighting used in hospitals.

However, current lighting apparatus used in hospitals, including veterinary hospitals and in veterinary practices do not address the additional problems that are specific to the management of clinical habitats for animal care. Current animal housings are primarily concerned with the security and comfort of the animal, but do not address other difficulties in ensuring recovery of the animal patient. It is important that natural daylight is replicated during day time for the animal patient, whilst ensuring the animal can rest well during the night and still be monitored without being disturbed throughout the day and night. In addition to adequate sleep aiding animal recovery, it is also important that the housing is kept clean of organic waste and other contaminants that may be detrimental to healing of the animal patient.

Lighting systems, such as that disclosed in US2017290124, for indoor livestock rearing in barns are concerned with controlling bodyweight and behaviour of livestock, whilst reducing the cost of illumination. Such known lighting systems are used to control lighting across an entire dwelling to optimise the growth and breeding of a large group of livestock. Such known lighting systems are not suited to tailored management of individual animal recovery in a clinical setting.

DETAILED DESCRIPTION

The present invention sets out to provide an improved veterinary lighting apparatus, which addresses the above-described problems for the management of clinical habitats for animal care.

In one aspect, the invention provides a veterinary lighting apparatus comprising:
a heat sink on which are supported a plurality of LEDs for emitting light radiation, wherein the plurality of LEDs comprises at least one white light LED-emitter; at least one blue light LED-emitter; and at least one red light LED-emitter; and
an activation means to switch on one or more of the white and/or blue and/or red light LED-emitters.

Preferably, the at least one white light LED-emitter emits radiation in the wavelength range of about 420 nm to about 750 nm.

Preferably, the at least one blue light LED-emitter emits radiation in the wavelength range of about 430 nm to about 450 nm.

Optionally, the at least one blue light LED-emitter emits radiation in the UV wavelength range of about 350-420 nm.

Preferably, the at least one red light LED-emitter emits radiation in the wavelength range of about 622 nm to about 780 nm.

Within this specification, the term "about" means plus or minus 20%; more preferably, plus or minus 10%; even more preferably, plus or minus 5%; most preferably, plus or minus 2%.

Preferably, the plurality of LEDs comprises a plurality of white light LED-emitters; a plurality of blue light LED-emitters; and a plurality of red light LED-emitters.

The veterinary lighting apparatus of the present invention significantly improves the recovery of the animal patient by assisting in the maintenance of a clean and secure animal housing that aids patient recovery. By maintaining a clean and hygienic environment the present invention improves the comfort and the recovery of the animal patient and reduces the labour required by veterinary practitioners or pet owners.

The white light allows for visibility so that the animal can see the surrounding environment and the veterinary practitioner can monitor the animal. Furthermore, the white light helps to regulate the circadian rhythm of the animal when natural daylight is not available by supporting the production of cortisol to keep the animal awake and alert during normal daylight hours. By allowing the animal patient to have clear visibility in daylight, patient anxiety is reduced.

The red light allows the veterinary practitioner to view the animal patient in recovery without disturbing the animal. Red light in the wavelength selected is not visible to cats, dogs, and other small mammal species, whilst being fully visible to the human eye allowing for clear observation of the animal in recovery. The veterinary practitioner can opt to allow the animal patient to have more rest; for example, after a surgical procedure or treatment, by relying on the red light to monitor the patient without use of bright lighting that would interfere with production of melatonin, which is important in regulation of sleep and circadian rhythm. The red light used is not for treatment of the patient but to allow for inspection without disturbing the animal patient.

The blue light emitted by the device highlights light organic waste within veterinary housing to allow for any necessary deep cleaning and sterilisation. This reduces the labour necessary to maintain the sterile environment that is essential to the animal patient's recovery because the blue light will highlight areas that would not be visible to the human eye in daylight. Greater visibility of any waste or contaminants improves the biosecurity and avoids the risk of cross-contamination if more than one animal is housed in the housing or if there are adjacent animal housings. This is particularly important to prevent the spread of contagious diseases. The wavelength of the blue light is harmless to the eyes of both the veterinary practitioner and the animal patient.

It is understood that the "veterinary" lighting apparatus of the present invention is beneficial for use by veterinary practitioners treating animals, but also has application for pet owners who are caring for animal patients.

Preferably, the veterinary lighting apparatus is a self-contained unit.

By provide the apparatus as a self-contained unit, the device is easy and safe to fit to new or existing animal housings, especially when the device is incorporated into a stack or similar arrangement of multiple housings; for example, as would be found in a veterinary practice or veterinary hospital. The single unit provides multiple lighting options that each offer an improvement to the recovery of an animal patient. By providing multiple lighting options in an integrated apparatus, the present invention maximises the speed, safety and effectiveness of the recovery of an animal patient.

Preferably, the veterinary lighting apparatus comprises a three-way selection switch.

Preferably, the activation means comprises a switch to switch on the at least one white light LED-emitter, or the at least one blue light LED-emitter, or the at least one red light LED-emitter.

The three-way selection switch of the present invention allows the veterinary practitioner to select between any one of white, red, or blue light depending on the animal patient's recovery requirements. Only one light colour is used at any one time so that the apparatus can be adapted to the specific requirements of the animal patient.

Preferably, the veterinary lighting apparatus comprises an aluminium heat sink.

Preferably, the heat sink comprises at least one curved surface.

Preferably, the heat sink comprises at least one curved surface having a plurality of ribs or protrusions.

Preferably, the heat sink comprises two pairs of four narrow protrusions separated by a pair of wide protrusions.

Preferably, the heat sink comprises recesses between each of the narrow protrusions that are shallower than the recess between the pair of wide protrusions.

The protrusions/ribs on the outer face of the heat sink increase the surface area from which heat generated by the lighting apparatus is emitted to maintain a safe operating temperature.

Preferably, the heat sink has a maximum depth of between about 10 mm and about 15 mm; more preferably, the heat sink has a maximum depth of about 12 mm.

Preferably, the apparatus has a length of between about 400 mm and about 600 mm; more preferably, the apparatus has a length of about 500 mm.

Preferably, the apparatus has a width of between about 35 mm and about 55 mm; more preferably, the apparatus has a width of about 45 mm.

Optionally, the veterinary lighting apparatus comprises at least one control means to allow activation of one of more of the white, blue and/or red light LED-emitters.

Preferably, the veterinary lighting apparatus comprises at least one control means to allow activation of one of the white or blue or red light LED-emitters at any one time.

By allowing the veterinary practitioner to select the correct lighting according to the animal patient's needs the recovery of the animal is significantly improved.

Optionally, the control means of the veterinary lighting apparatus comprises a timer.

A timer can be used to pre-set the lighting requirements according to the animal patient's needs so that the recovery of the patient can be improved without requiring the veterinary practitioner to manually select the required colour of lighting.

Preferably, the veterinary lighting apparatus comprises at least one securing means for fixing the lighting apparatus to an animal housing or cage.

Preferably, the securing means comprises at least one adhesive layer.

Preferably, the securing means comprises at least one adhesive layer and a removable backing liner.

Preferably, the veterinary lighting apparatus is retrofittable to an animal housing.

Preferably, the animal housing is a glass enclosure having a vinyl outer covering, and/or an enclosure comprising a stainless-steel cage and/or an aluminium housing having at least one glass window, and/or an aluminium housing having a toughened safety glass window.

The apparatus of the present invention can be moved between animal housings and can be retrofitted to an existing veterinary housing.

In a further aspect, the invention provides an animal housing comprising the veterinary lighting apparatus as previously described.

Preferably, the animal housing comprises an elongate opening into which the veterinary lighting apparatus as previously described is fitted.

Preferably, the animal housing comprises an elongate opening into which the veterinary lighting apparatus as previously described is secured by adhesive.

Preferably, the animal housing comprises an elongate opening into which the veterinary lighting apparatus as previously described is fitted and a console on an external face of the animal housing to which a three-way switch is secured.

In a further aspect the invention provides a method of lighting a veterinary housing; comprising:
selecting between a white, a blue and a red light LED-emitter to emit light from the veterinary lighting apparatus as previously described;
switching on the selected radiation source; and
providing light to the interior of the veterinary housing.

Preferably, the lighting apparatus is secured to the animal housing.

For the purposes of clarity and a concise description, features are described herein as part of the same or separate embodiments; however, it will be appreciated that the scope of the invention may include embodiments having combinations of all or some of the features described.

BRIEF DESCRIPTION OF THE FIGURES

The invention will now be described by way of example with reference to the accompanying drawings, in which:

FIG. 1 is a view from below of the veterinary lighting apparatus in accordance with a first embodiment of the present invention, wherein the view from below is understood to show the light emitting surface of the apparatus;

FIG. 2 is a view from above of the veterinary lighting apparatus of FIG. 1;

FIG. 3 is a side view of the veterinary lighting apparatus of FIGS. 1 and 2;

FIG. 4 is a perspective view from a first end of the veterinary lighting apparatus of FIGS. 1 to 3;

FIG. 5 is a schematic view of the electronic connections of the veterinary lighting apparatus of the present invention;

Referring to FIG. 1, the veterinary lighting apparatus 1, comprises a heat sink 3 on which is mounted a series of LEDs 5. FIG. 1 shows the lower surface 7a of the apparatus 1, which in use directs light radiation from the apparatus 1 into a veterinary housing (not shown) in the interior of which an animal patient is housed. The veterinary housing 25 is a toughened safety glass housing with a hinged toughened safety glass door, as shown in FIG. 6, or a cage, a glass cage, or any similar housing for an animal. The veterinary housing is understood to be for care of animals, including, cats, dogs, and other small mammals, such as, rabbits, mice, rats, guinea pigs, hamsters, and gerbils.

As shown in FIG. 6, the veterinary lighting apparatus 1 is configured to be integrated into a modular housing 25 comprising a plurality of enclosures, each separated from adjacent enclosures and each enclosure having its own glass door 27.

The lower surface 7a of the veterinary lighting apparatus 1 comprises at least two adhesive strips 9. Prior to use, the adhesive strips 9 are covered by a backing liner (not shown) that is removed prior to use to expose the adhesive for securing the apparatus 1 to an upper surface of a veterinary housing so that, when switched on, light from the LEDs 5 radiates into the interior of the housing.

Figure 6:
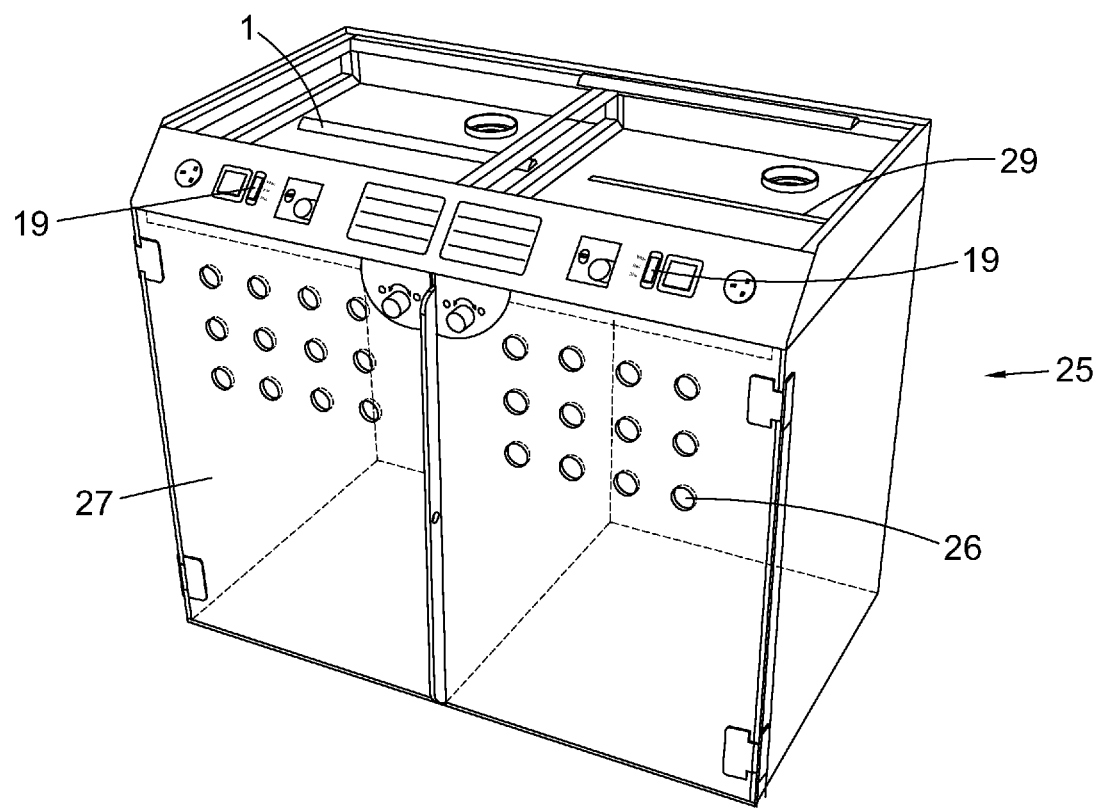
FIG. 6 is a perspective view of an animal housing to which the veterinary lighting apparatus of the present invention is secured.

Referring to FIG. 6, in a preferred embodiment, the housing 25 is a glass cage having a vinyl outer covering and ventilation holes 26 in the hinged glass door 27. An elongate opening or channel 29 is cut out of the vinyl outer covering on the top surface of the housing 25 and the veterinary lighting apparatus 1 is placed into the channel 29 so that light is emitted into the interior of the housing 25. The lighting apparatus 1 does not interfere with the security of the housing and the apparatus 1 cannot come into contact with an animal housed therein. In alternative embodiments, the veterinary lighting apparatus is attached to the housing by a bracket.

Referring to FIG. 6, for a veterinary housing 25 comprising multiple enclosures, each having separate access through a transparent door 27, a separate veterinary lighting apparatus 1 can be mounted to each enclosure to allow for separate control of the radiation emitted into each enclosure. Thus, the timing and wavelength of radiation emitted into each enclosure can be carefully controlled to optimise the recovery of the small animal housed in the enclosure, which can be planned by a veterinary practitioner. Alternatively, if multiple small animals are housed in adjacent enclosures and the treatment required is the same for multiple enclosures, a single veterinary lighting apparatus can be mounted across multiple enclosures to illuminate multiple enclosures simultaneously.

In a preferred embodiment, the apparatus 1 has a length of 500 mm and a width of 45 mm. Referring to FIGS. 1 and 2, the upper surface 7b of the apparatus 1 comprises a heat sink 3, which is aluminium and faces away from the interior of the animal housing when the apparatus is secured to the animal housing. The heat sink 3 is configured to maximise the dissipation of heat from the device and to maximise air flow to carry heat away from the circuitry.

Referring to FIGS. 2 and 3, the heat sink 3 comprises the flat lower surface 7a on which the LEDs 5 are mounted and a curved upper surface 7b, which comprises a series of shaped protrusions 7c and has a maximum depth of 12 mm. In the example shown, the cross-section of the apparatus 1 corresponds to a circular segment. The apparatus has a cross-section having a shape which is bounded by an arc of a circle, wherein the arc of the circle is less than 180 degrees, and the endpoints of the arc are connected by a chord. In the example shown, the arc of the cross-section is about 120 degrees.

Referring to FIG. 3, in the example shown, the heat sink 3 comprises two pairs of four narrow protrusions separated by a pair of wide protrusions. The recesses between each of the narrow protrusions are shallower than the recess between the wide protrusions. This particular arrangement of narrow and wide protrusions has been found to be particularly effective in relation to the present invention.

Referring to FIGS. 1 and 4, the apparatus 1 comprises a first set of white light LEDs 5a to emit white light having a wavelength of between about 420 nm to about 750 nm. The white light LEDs 5a emit radiation comparable to daylight to ensure clear visibility for both the veterinary practitioner and the animal patient. A second set of red LEDs 5b emit red light having a wavelength of between about 622 nm to about 780 nm. A third set of blue/ultra-violet LEDs 5c emit blue/ultra-violet light in a wavelength of between about 430 nm to about 450 nm. The white, red, and blue LEDs 5a, 5b, 5c are arranged consecutively along the length of the apparatus 1. A white, red, and blue LED are followed by a further white, red and blue LED in sets of three LEDs 5a, 5b, 5c. Each LED 5a, 5b, 5c and each LED set is equidistant from each other along the length of the apparatus 1.

Referring to FIG. 4, the apparatus 1 is powered by AC mains power 17 and the apparatus comprises an AC to DC converter 21. As shown in FIGS. 4 and 5, the apparatus comprises an on/off switch and a three-way channel selector switch 19 with LED channel connections 23 to the red, blue, and white LED light sources 5b, 5c, 5a.

Figure 7:
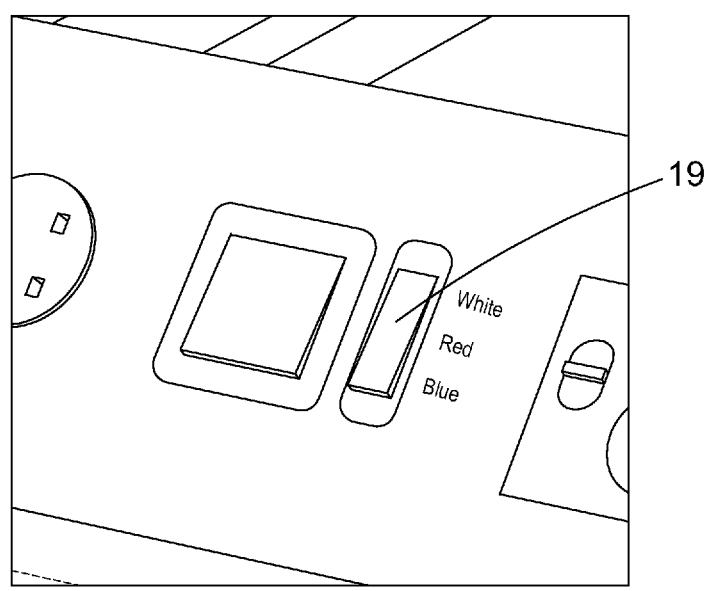
FIG. 7 is an enlarged view of the three way switch to control the veterinary lighting apparatus.

Referring to FIGS. 1, 6 and 7, the three-way selector switch 19 allows for manual selection of which LED light source 5a, 5b, 5c is to be turned on to radiate the required lighting colour into the housing 25. Only one light colour is used at any one time so that the apparatus can be adapted to the specific requirements of the animal patient. The switch 19 is provided in a console on the exterior of the housing 25. In an alternative embodiment, the required lighting colour can be controlled by a timer so that the required light is automatically switched on.

In use, the veterinary practitioner manually selects the required light source 5a, 5b, 5c according to their knowledge of the condition and the needs of the animal patient with only one of each light colour used at any one time. The white light LEDs 5a are switched on for use during daylight hours to help stimulate production of the hormone, cortisol, so that the animal patient can regulate their body clock even if natural daylight is not available. The red light LEDS 5b are manually switched on by the veterinary practitioner to view the animal patient in recovery without disturbance to their rest. The veterinary practitioner can monitor the animal to check their recovery, but the animal patient will not be aware of the red light. The blue light LEDs 5c are manually switched on for inspection of the interior of the housing. The blue light highlights light organic waste because the blue light reflects from the material, including faeces, urine, blood, mucus, and other bodily fluids within the veterinary housing. The veterinary practitioner can then clean and sterilise any contaminated areas.

In an alternative embodiment, a timer switch is set to switch on the white light LEDs during pre-set hours; for example, between 7 am and 6 pm. The red recovery LEDs 5b are switched on for use during non-daylight hours; for example, between 6 pm and 7 am.

The above-described embodiment has been given by way of example only, and the skilled reader will naturally appreciate that many variations could be made thereto without departing from the scope of the claims.

The invention claimed is:

1. A veterinary lighting apparatus comprising:
   a heat sink on which are supported a plurality of LEDs for emitting light radiation, wherein the plurality of LEDs comprises at least one white light LED-emitter; at least one blue light LED-emitter; and at least one red light LED-emitter; and
   an activation means to switch on one or more of the white and/or blue and/or red light LED-emitters,
   wherein the veterinary lighting apparatus is configured to support the circadian rhythm of an animal such that the white light LED-emitter is switched on during daylight hours and the red light LED-emitter is switched on to allow the animal to be monitored or inspected without using the white light LED-emitter, and wherein the blue light LED-emitter is configured to highlight organic waste.

2. The veterinary lighting apparatus according to claim 1, wherein the at least one white light LED-emitter emits radiation in the wavelength range of about 420 nm to about 750 nm.

3. The veterinary lighting apparatus according to claim 1, wherein the at least one blue light LED-emitter emits radiation in the wavelength range of about 430 nm to about 450 nm.

4. The veterinary lighting apparatus according to claim 1, wherein the at least one red light LED-emitter emits radiation in the wavelength range of about 622 nm to about 780 nm.

5. The veterinary lighting apparatus according to claim 1, wherein the plurality of LEDs comprises a plurality of white light LED-emitters, a plurality of blue light LED-emitters and a plurality of red light LED-emitters.

6. The veterinary lighting apparatus according to claim 1, wherein the veterinary lighting apparatus is a self-contained unit.

7. The veterinary lighting apparatus according to claim 1, wherein the veterinary lighting apparatus comprises a three-way selection switch.

8. The veterinary lighting apparatus according to claim 1, wherein the activation means comprises a switch to switch on the at least one white light LED-emitter or the at least one blue light LED-emitter or the at least one red light LED-emitter.

9. The veterinary lighting apparatus according to claim 1, wherein the heat sink comprises at least one curved surface.

10. The veterinary lighting apparatus according to claim 1, wherein the heat sink comprises two pairs of four narrow protrusions separated by a pair of wide protrusions.

11. The veterinary lighting apparatus according to claim 1, wherein the heat sink comprises recesses between each of the narrow protrusions that are shallower than the recess between the pair of wide protrusions.

12. The veterinary lighting apparatus according to claim 1, wherein the apparatus has a length of between about 400 mm and about 600 mm and/or wherein the apparatus has a width of between about 35 mm and about 55 mm.

13. The veterinary lighting apparatus according to claim 1, wherein the veterinary lighting apparatus comprises at least one control means to allow activation of one of the white or blue or red light LED-emitters at any one time.

14. The veterinary lighting apparatus according to claim 1, wherein the veterinary lighting apparatus comprises at least one control means to allow activation of one or more of the white, blue and/or red light LED-emitters.

15. The veterinary lighting apparatus according to claim 1, further comprising at least one control means comprising a timer.

16. The veterinary lighting apparatus according to claim 1, wherein the veterinary lighting apparatus comprises at least one securing means for fixing the lighting apparatus to an animal housing or cage.

17. The veterinary lighting apparatus according to claim 16, wherein the animal housing is a glass enclosure having a vinyl outer covering.

18. A veterinary lighting apparatus according to claim 1, wherein the veterinary lighting apparatus is retrofittable to an animal housing or cage.

19. An animal housing comprising an elongate opening into which the veterinary lighting apparatus of claim 1 is fitted.

20. The animal housing according to claim 19, further comprising a console on an external face of the animal housing to which a three-way switch is secured.

21. A method of operating the veterinary lighting apparatus of claim 1, comprising
   switching on the white light LED-emitter during daylight hours to support the circadian rhythm of an animal;
   switching on the red light LED-emitter to allow the animal to be monitored or inspected without using the white light LED-emitter; and
   switching on the blue light LED-emitter to highlight organic waste.

* * * * *